United States Patent [19]

Isaacson

[11] Patent Number: 4,920,490
[45] Date of Patent: Apr. 24, 1990

[54] PROCESS AND APPARATUS FOR DISTINGUISHING CONDUCTIVITIES BY ELECTRIC CURRENT COMPUTED TOMOGRAPHY

[75] Inventor: David Isaacson, Latham, N.Y.

[73] Assignee: Rensselaer Polytechnic Institute, Troy, N.Y.

[21] Appl. No.: 149,407

[22] Filed: Jan. 28, 1988

[51] Int. Cl.$^5$ .............................................. A61B 5/05
[52] U.S. Cl. ................................ 364/413.13; 128/734
[58] Field of Search ...................... 364/413.13, 413.15, 364/413.02; 128/734

[56] References Cited

U.S. PATENT DOCUMENTS

| 4,291,708 | 9/1981 | Frei et al. | 128/734 |
| 4,486,835 | 12/1984 | Bai et al. | 364/413.13 |
| 4,539,640 | 9/1985 | Fry et al. | 364/413.13 |
| 4,729,385 | 3/1988 | Juncosa et al. | 128/734 |
| 4,794,934 | 1/1989 | Motoyama et al. | 364/413.02 X |

OTHER PUBLICATIONS

Lytle et al., "An Impedance Camera: A System for Determining the Spatial Variation of Electrical Conductivity", Lawrence Livermore Report UCRL-S2413, 1978.
Seager et al., "Full-Wave Computed Tomography-Part 2: Resolution Limits" IEEE Proceedings, vol. 131, PTA, No. 8, 11/84.
Seager et al., "Full-Wave Computed Tomography-Part 4: Low Frequency Electric Current CT", IEEE Proceedings, vol. 132, PTA, No. 7, 11/85.
D. Isaacson, "Distinguishability of Conductivities by ECCT", Jun. 1986, IEEE Transaction on Medical Imaging, vol. MI-5, No. 2, pp. 91-95.
Hendersen et al.; "An Impedance Camera"; IEEE Trans. Biomed Eng., vol. BME-25, No. 3, pp. 250-254, May 1978.
Murai et al.; "Electrical Impedance CT ... "; BME-32, No. 3, pp. 177-184, 3/85.
Bates et al.; "A Limitation on Systems for Imaging ... "; BME-25, No. 3, pp. 250-254, 5/78.

Primary Examiner—Jerry Smith
Assistant Examiner—Steven G. Kibby
Attorney, Agent, or Firm—Notaro & Michalos

[57] ABSTRACT

A method and apparatus for an electric current computed tomography system having an array of electrodes determines the best pattern of currents to apply to the electrodes based on the precision of the system for distinguishing between a known conductivity in a body and an unknown conductivity. An arbitrary current pattern is first applied to the array, which is at the surface of the body. Measurements are then taken for the resulting voltage pattern of the unknown conductivity. Calculations are then made to determine the calculated voltage pattern for the selected conductivity. The absolute value of the difference between the calculated and measured voltage patterns are then taken and, from this, a new current pattern is calculated. If the difference between the new current pattern and the arbitrary current pattern is less than the precision of the system, the arbitrary current pattern is applied to the electrodes. More likely, however, the difference will be greater than the precision. In this case, the new current pattern is applied to the electrodes and the measurements and calculations are repeated to generate a still further new current pattern. The difference between the previous and the new current pattern is then taken and again compared to the precision of the system. By repeating this process, the best current pattern is eventually reached.

3 Claims, 9 Drawing Sheets

PROCESS AND APPARATUS FOR DISTINGUISHING CONDUCTIVITIES BY ELECTRIC CURRENT COMPUTED TOMOGRAPHY

FIELD AND BACKGROUND OF THE INVENTION

The present invention relates in general to the field of electric current computed tomography or ECCT, and, in particular, to a new and useful method and apparatus for determining which pattern of current to apply to the surface of a body in order to best distinguish an unknown conductivity distribution within the body from a known conductivity distribution.

Various interior regions and organs of the human body are known to have different conductivity. Knowledge concerning the patterns of this conductivity can be used as a clinical tool. Differences in conductivity can indicate, for example, the presence of breast tumors.

U.S. Pat. No. 4,539,640 to Fry et al discloses a system and method of impedance imaging which utilizes an array of electrodes that are applied to the outer surface of a torso to be examined in a non-invasive manner. Currents are applied to the electrodes and resulting voltages are measured. Calculations are then made to construct an image for impedances in the body. This reference, however, does not teach how a best possible distribution of currents can be applied to the electrodes for best distinguishing the electrical properties of different areas in the body.

An apparatus and method for detecting tumors in living tissue is disclosed in U.S. Pat. No. 4,291,708 to Frei et al, which determine dielectric constants of various local regions in the tissue. This apparatus and method is drawn primarily to detecting tumors in breast tissue. It does not teach how one should go about selecting a current pattern for application to a plurality of electrodes for determining the electrical properties of the human tissue.

U.S. Pat. No. 4,486,835 to Bai et al teaches an ECCT technique, which utilizes an array of electrodes to be applied to an area of the human body and supplied with electric voltages. Currents produced by these voltages are then measured to calculate the electrical properties at a plurality of locations in the body for the purpose of producing a visual representation of the electrical properties.

So-called impedance cameras and other techniques for imaging patterns of electrical properties within the human body and other objects are disclosed in:
(1) R. J. Lytle and K. A. Dines, "An impedance camera: a system for determining the spatial variation of electrical conductivity," Lawrence Livermore Laboratory Report, UCRL-52413, 1978.
(2) R. P. Henderson and J. G. Webster, "An impedance camera for spatially specific measurements of the thorax," IEEE Trans. Biomed. Eng. Vol. BME-25, No. 3, p. 250–254, May 1978.
(3) R. H. Bates, G. C. McKinnon, and A. D. Seager, "A limitation on systems for imaging electrical conductivity distributions," IEEE Trans. Biomed. Eng., Vol. BME-27, p. 418–420, July 1980.
(4) T. Muari and Y. Kagawa, "Electrical impedance computed tomography based on a finite element model," IEEE Trans. Biomed Eng. Vol. BME-32, No. 3, p. 177–184, March 1985.

SUMMARY OF THE INVENTION

The present invention provides a method and apparatus for automatically determining the best pattern of currents to apply to the electrodes of an array in an electric current computed tomography (ECCT) system. In an ECCT system, having a finite precision, an object of the invention is to find the best current pattern which permits the system to distinguish between an unknown conductivity $\sigma$ inside the body from a given conductivity s.

In order for an ECCT system to image a conductivity $\sigma$, it must be able to distinguish it from all conductivities, $s = s(p)$, in some class of functions. In other words, there must be some current $j_l$ whose voltage $v(p;\sigma,j_l)$ differs from voltage for the other conductivities $v(p;s,j_l)$, by more than the precision of the ECCT system. Otherwise, the system cannot distinguish $\sigma$ from s (where p is a point in the body).

In a paper by the inventor (D. Isaacson, "Distinguishability of Conductivity by Electric Current Computed Tomography", IEEE Transaction of Medical Imaging, Vol. MI-5, No. 2, June 1986), it was shown what the best pattern of current $j_l$ is to distinguish $\sigma$, the unknown conductivity from s, a known conductivity.

The present invention provides an automatic process by which an ECCT system can find this best pattern of current. The present invention solves the problem of whether or not the ECCT system can distinguish the unknown conductivity from the selected known conductivity. The invention also yields the best pattern of current for distinguishing these two conductivities.

While the present invention is particularly useful for non-invasive medical diagnosis, it can also be utilized for imaging the interior of materials other than living tissue, for geophysical imaging of the earth and oceans and other fields where imaging changes in conductivity would be useful.

The method of the present invention automatically finds the best current $j_l$ to distinguish the unknown conductivity $\sigma$ inside a body from a given or selected conductivity s, by following the steps of:
(a) Guessing a current $j^o(p)$ and applying it to the surface of the body;
(b) Measuring and recording the resulting voltage for the unknown conductivity $v(p; \sigma, j^o)$;
(c) Calculating or analytically computing the voltage for the given conductivity, $v(p; s, j^o)$;
(d) Numerically calculating the difference between the measured and computed voltages;

$$y(1) = (v(p;\sigma,j^o) - v(p;s,j^o))$$

(where p is a point in the body)

$$\text{and } j^l = y(1) / \| y(1) \|$$

(e) If $j^l(p)$ and $j^o(p)$ differ by less than the precision of the ECCT system, then $j_l = j^l(p)$.

If not, the guessed current $j^o(p)$ is changed to the new current $j^l(p)$ and applied as a new current in step (a) above to repeat the process. Likewise, the process is repeated until the best current pattern $j_l$ is found to match the precision of the ECCT system. To better understand the present invention, a description of the forward and inverse problems to be solved will first be given. Letting B denote a body and S its surface, it is first assumed that B is a linear conductor with scalar conductivity $\sigma = \sigma(p)$, where p is a point in the body as in the foregoing equations.

The voltage or potential $U = U(p)$ is assumed to satisfy $$\nabla \cdot \sigma \nabla U = 0$$

in B. The current density vector is denoted by $J = J(p)$ and is given by $$J = -\sigma \nabla U.$$

In the forward problem, it is assumed that $\sigma$, and the normal component of the current density vector on the body's surface S are given.

In other words, on S we are given $$J \cdot n = -\sigma \frac{\partial U}{\partial n} = j$$

where n denotes the unit outward normal vector on S. If one specifies U at one point in B, and one chooses a j for which $$\int_S j \, dA = 0$$

then there is a unique solution $U(p)$ to the preceding equations. Its restrictions to the boundary S is denoted by $$V = V(p) \equiv U(p),$$

for p on S.

Thus, the forward problem is to find the voltage V on the body's surface S, given the conductivity $\sigma$ and current j. To emphasise that the voltage V is a linear functional of j and a non-linear functional of $\sigma$, one writes $$V = V(p;\sigma,j).$$

This forward problem can be solved numerically by finite difference or finite element methods.

The inverse problem is to find the conductivity $\sigma$ in B from a knowledge of $$V_k = V(p;\sigma,j_k)$$

for a sequence of currents $j_k$, $k = 1,2,3, \ldots$

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

The present invention is designed primarily for application to biological systems. As noted above, however, it also has applications in other fields where an image of conductivity patterns within a body is desired.

The most promising application for the present invention, on biological systems, is for the thorax of a human body. For this reason, an invitro idealized model of the thorax is used to demonstrate the invention.

Figure 1:
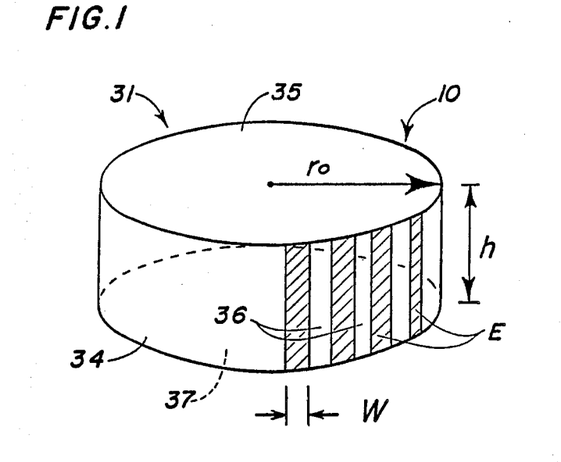
FIG. 1 is a perspective view of an idealized model of a thorax in the form of a tank used to demonstrate the present invention.

FIG. 1 is a schematic representation of a cylindrical tank generally designated 31 having a plastic cylindrical wall 34, a closed bottom 37 and a top 35. Thirty-two electrodes E are distributed in an array generally designated 10 around the tank 31. Each electrode is fashioned from a titanium plate having a platinum-iridium surface. These electrodes are arranged on the interior surface of the cylindrical plastic tank 31. The tank has a radius $r_o$ of 15 cm and a height or depth h of 6.5 cm. The electrodes are each 28.4 mm wide (W) and leave a 1 mm gap 36 between adjacent electrodes. Each electrode extends the full height h of the tank.

To demonstrate the present invention, the tank 31 was filled to a depth of 36 mm with different saline solutions having various electrical conductivities over the range of interest. Targets with different geometries and conductivities were then placed in the tank. Metal or plastic targets were used for conductivity of infinity (conducting) and zero (insulating). When conductivity similar to that of the bath in the tank were desired, mixtures of agar in saline were used to produce gelatine-like structures of desired geometry and conductivity.

To better understand the theory of the inventive process, consider a body B whose internal conductivity at a point p is $\sigma(p)$ and which is surrounded by a surface S having area A. If L electrodes are then placed on the surface S, the area available for each electrode is A/L. In practice, the electrodes cannot cover the surface, which must have inter-electrode gaps. If f is the fraction of the available area covered by the electrodes, than fA/L is the area of each electrode.

For $l = 1,2, \ldots, L$; $I_l^k$ denotes the $k^{th}$ current applied to the $l^{th}$ electrode and $V_l^k$ denotes the $k^{th}$ voltage that results on the $l^{th}$ electrode.

In the tank, shown in FIG. 1, S is a cylinder of radius $r_o$ with L electrodes E placed on its sides of height h and width.

$$W = f \cdot r_0 \cdot 0.2\pi/L.$$

When the cylinder is filled with saline of conductivity $\sigma_o$ to a height h and currents $I_l^k$ are applied to the electrodes E centered at $\theta_l = l \cdot 2\pi/L$, a current density $j^k = j^k(\theta)$, that is independent of depth, results on S.

Generally, this current density has a fourier series representation $$j^k(\theta) = \sum_{n=1}^{\infty} c_n^k \cos n\theta + S_n^k \sin n\theta$$

$$\text{where } c_n^k = \frac{1}{\pi} \int_0^{2\pi} j^k(\theta) \cos n\theta \, d\theta$$

$$\text{and } S_n^k = \frac{1}{\pi} \int_0^{2\pi} j^k(\theta) \sin n\theta \, d\theta$$

This current density results in voltages $V_l^k = V_l^k(\sigma_o)$.

Let $V_l^k(s)$ denote the voltages that the $k^{th}$ current would produce on the $l^{th}$ electrode when a cylinder of radius r, depth h, and conductivity $\sigma$ is centered in the previous saline filled tank or phantom.

The voltage difference between homogeneous and centered phantoms, $\delta V_l^k$ is then approximately given by $$\delta V_l^k = V_l^k(\sigma_o) - V_l^k(s) \quad (1)$$

where $$p_n^k = (r_o/\sigma_o n) \cdot (2\mu R^{2n})/(1+\mu R^{2n})$$

and $$\mu \equiv (\sigma - \sigma_o)/(\sigma + \sigma_o)$$

$$R \equiv r/r_o$$

Figure 2:
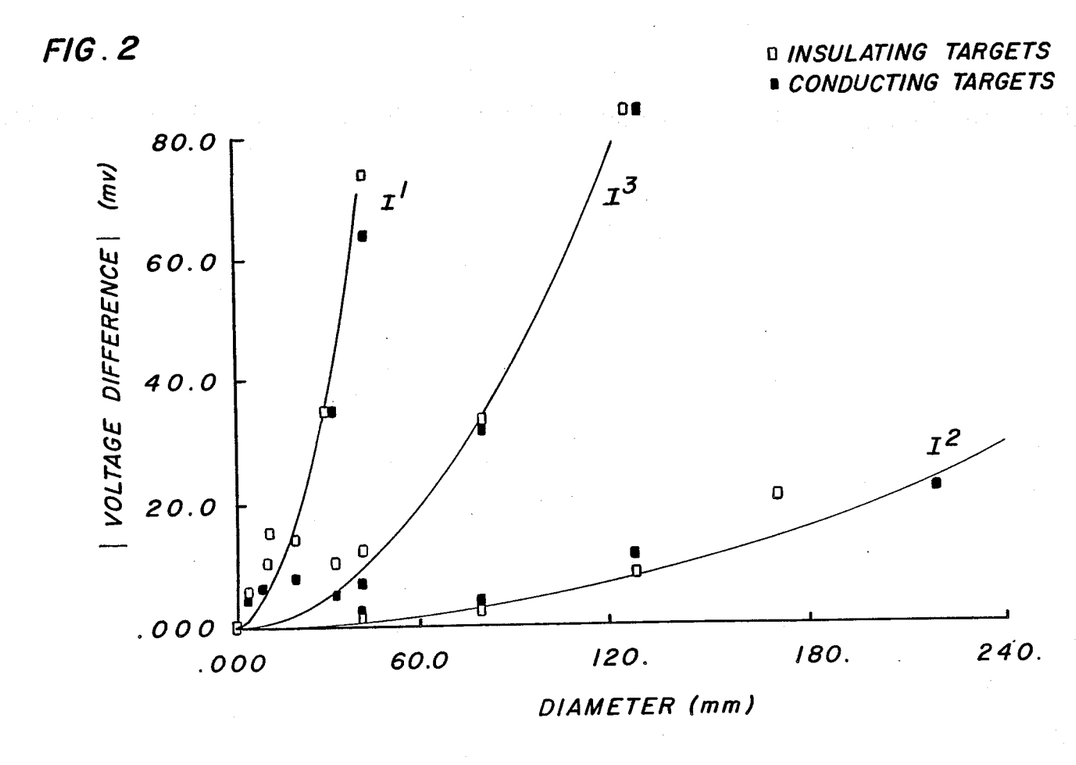
FIG. 2 is a graph plotting absolute voltage difference for electrodes around the tank against the diameter of target objects in the tank for demonstrating the present invention.

This formula (1) is compared with experiments illustrated in FIG. 2 for the currents (in mA)

$$I_l^1 = 5 \cos k\theta_l$$

$$I_l^2 = \begin{bmatrix} 5 \text{ if } l = 1 \\ -5 \text{ if } l = 2 \\ 0 \text{ if } l \neq 1 \text{ or } 2 \end{bmatrix}$$

$$I_l^3 = \begin{bmatrix} 5 \text{ if } l = 1 \\ -5 \text{ if } l = 17 \\ 0 \text{ if } l \neq 1 \text{ or } 17 \end{bmatrix}$$

The cosine pattern $I^l$ yields the largest voltage differences and enables one to distinguish smaller centered targets than the other patterns.

A centered cylindrical conductor of radius r can be distinguished from a uniform background by the current pattern $I^k$ only if the maximum voltage difference, $\max_l |\delta V_l^k| \geq \epsilon_v$ where $\epsilon_v$ is the smallest voltage difference the system can reliably measure.

When L is large and f is approximately one, it follows from (1) that for the cosine current pattern $I^1$ this is the case if $$r \geq r_b \equiv \left[ \frac{f\pi h}{5L} \sigma_0 \epsilon_v \right]^{1/2} r_o \quad (2)$$

For the single current $I^2$ applied between a pair of adjacent electrodes:

$$r \geq r_a \equiv [4 \sin(f\pi/L) \sin(\pi/L)/\pi]^{-\frac{1}{2}} r_b. \quad (3)$$

For the single current $I^3$ applied between opposite electrodes:

$$r \geq r_p \equiv [4 \sin(f\pi/L)/\pi]^{-\frac{1}{2}} r_b. \quad (4)$$

Figure 3:
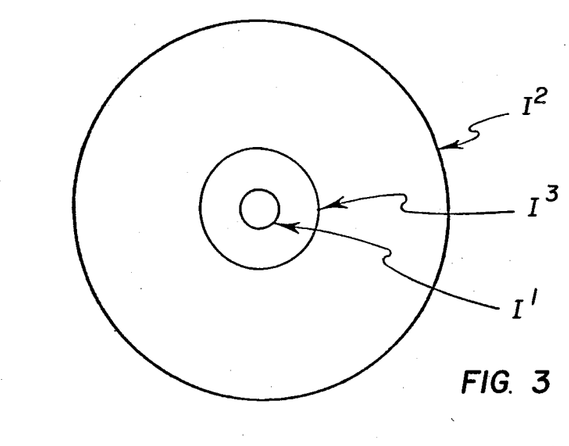
FIG. 3 is an illustration showing the relative sizes of the smallest non-homogeneous area distinguishable from a uniform background for three current patterns applied to the electrodes around the tank.

Here $2r_b$, $2r_a$ and $2r_p$ yield the diameters of the smallest centered, conducting cylinders that can be distinguished from a uniform background. When $r_o = 15$ cm, $\sigma_o^{-1} = 350 \, \Omega$-cm, L=32, h=3.6 cm. and $E_v = 5$ mV the respective diameters are 0.9, 2.6 and 8.3 cm as shown in FIG. 3 and confirmed by experiment.

In general, one measures the ability of a current pattern $I^k = (I_1^k, I_2^k, \ldots I_L^k)$, to distinguish between two conductivities $\sigma$ and by a single number, the "distinguishability $\delta$" where $$\delta = \delta(\sigma, s; I^k) \equiv \frac{\left[ \sum_{l=1}^{L} (v_l^k(\sigma) - V_l^k(s))^2 \right]^{1/2}}{\left[ \sum_{l=1}^{l} (I_l^k)^2 \right]^{1/2}}.$$

We define $I^*$ to be a "best" pattern of current to distinguish o from $s$ if $I^*$ maximizes the distinguishability, i.e.

$$\delta(\sigma, s; I^*) = \max_I \delta(\sigma, s; I)$$

For the previous example, it can be proven that $I^1$ is a "best" pattern. In general, the best pattern depends on $\sigma$ and s and cannot be known in advance.

Figure 7:
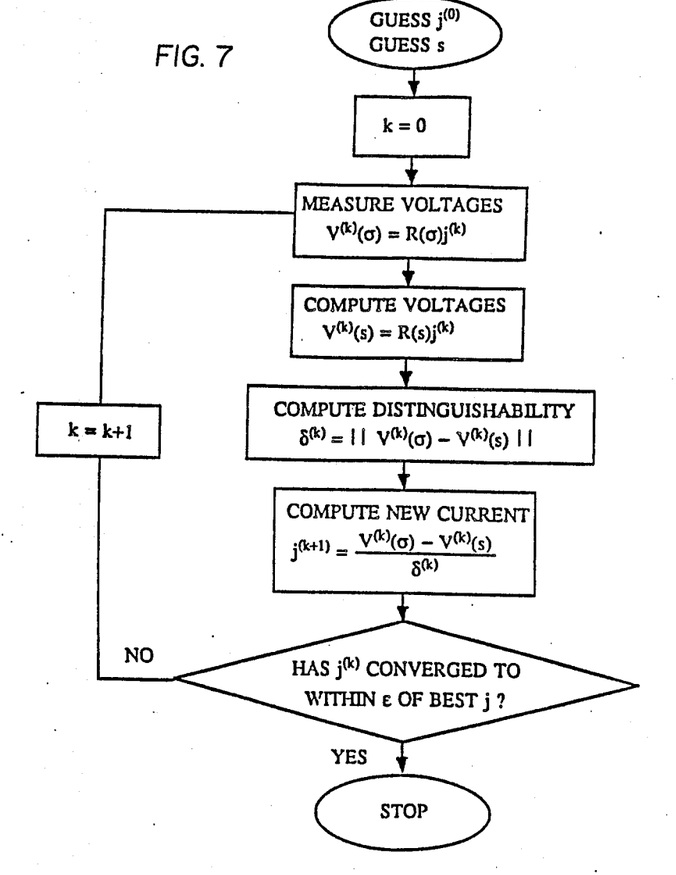
FIG. 7 is a flow chart showing the adaptive current selecting scheme of the present invention.

The inventive process for producing the "best" I to distinguish $\sigma$ from s is shown in FIG. 7 where the process is illustrated in terms of current density j. FIG. 7 illustrates the following steps of the invention:
(a) Guess any $I^k$ for $k=0 (J^{(o)})$.
(b) Measure and compute $V^k(\sigma)$ and $V^k(s)$.
(c) Compute $$\delta v^k \equiv v^k(\sigma) - v^k(s)$$

$$||\delta V^k|| = \left[ \sum_{l=1}^{L} (\delta V_l^k)^2 \right]^{1/2}$$

and compute $$I^{k+1} = \delta V^k / ||\delta V^k||$$

(d) If $||I^{k+1} - I^k|| \leq \epsilon$ (minimum current difference specifiable) stop, otherwise set $k = k+1$, and go to step (b).

Figure 4:
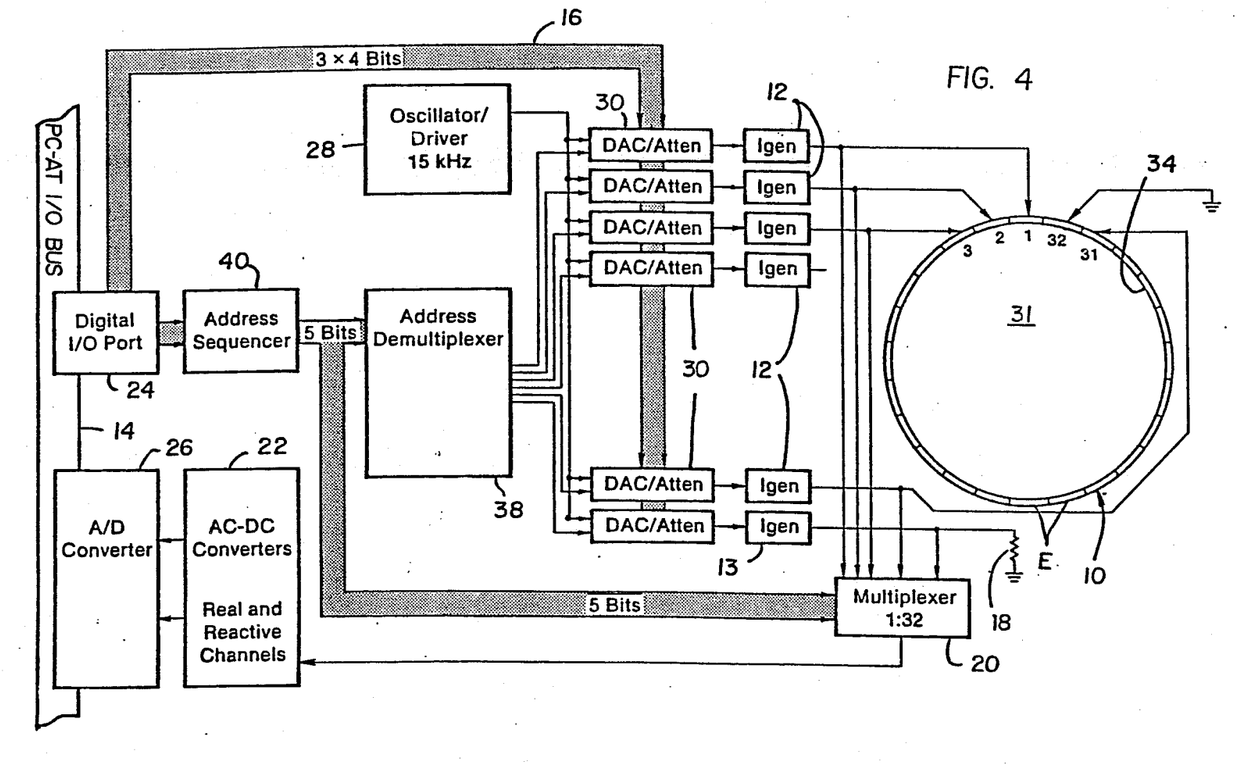
FIG. 4 is a block diagram showing the apparatus used to demonstrate the present invention in conjunction with the thorax model.

In order to be able to produce these "best" current patterns, the instrument of FIG. 4 is used.

The overall system architecture was designed for maximum flexibility with a minimum of special-purpose hardware. The system is an array of thirty-two current generators 12, 13, each of which has a separately programmable output level. A single voltmeter 22 is attached sequentially through a multiplexer 20 to each electrode E of array 10 in tank 31 for measurement purposes. This special-purpose hardware is connected to a microcomputer 14 (e.g. an IBM PC-AT) through a general-purpose analogue and digital interface board 24, 26 (e.g., a Data Translation DT2800). Synchronization between the instrument and software is accomplished by having the software write clock signals to the digital output port 24. A stable sinusoidal oscillator 28, at 15 kHz is included in the instrument.

The 15 kHz oscillator output is buffered and directed to each of thirty-two current generators 12, 13. Each generator is based upon a three-amplifier configuration, using type LF 412 op-amps. The output of each generator 12, 13 is coupled through a 1 (mu)F capacitor directly to the output electrode. The maximum load for the current generators is 1,000 ohms at 5 mA rms. With an output current sensing resistor of 432 ohms, the op-amp output voltage ranges between about 2-7 V rms for load resistances between 0 and 1,000 ohms. Input to each current generator is obtained from a multiplying digital-to-analogue converter (DAC) (e.g., an AD 7549), operating as a digitally controlled attenuator 30. The analogue input signal to the DAC reference terminal is the 15 kHz output from the oscillator 28. Digital input to the DAC is obtained from the digital output port 24 of the computer through the DT 2800 board. Some complexity is introduced here since the DAC used requires a sequence of three "nibbles" of four bits each to acquire a full 12 bit word it then converts. This requirement is handled by the controlling software and on-board digital sequencer 40. The DAC circuit is configured as a 4 quadrant converter, so that currents of either polarity and between 0–5 mA rms amplitude may be produced by any of the thirty-two current generators.

One of the electrodes of tank 31 is grounded. For this reason, only thirty-one current generators 12 are actually needed to implement the 32 electrode scheme. The thirty-second current generator 13 is connected to a precision fixed resistor 18, and serves as a reference and test channel.

The digital multiplexer 20 selects one of the 32 electrodes and connects it to the input stage of the voltmeter 22. This meter consists of a two-stage high-pass filter ($f_{co}$ — 1.9 kHz), followed by a synchronous full-wave demodulator (AD 630). The demodulator is an active switching device synchronized with the oscillator output through an adjustable phase shifter, which compensates for small phase shifts elsewhere in the circuit.

The detector switches at the exact zero crossings of the real component of the voltage signal.

A two-stage low-pass filter having poles or cutoff frequencies of 177 Hz and 1770 Hz then produces a ±5 volt DC signal proportional to the electrode voltage amplitude. This voltage is sampled by the analogue-to-digital convertor (ADC) 26 of the interface board (DT 2801/5716), which has 16 bit resolution, programmable gain, and is under software control. The filter has a calculated attenuation at 24 kHz of 65.0 db, and a calculated ripple of 4 millivolts peak with a 7 volt rms input.

A single digital sequencer 40 addresses both the current generator 12, 13 and the demultiplexer 20 for the voltmeter 22. Under software control, a master reset signal assures that the sequence begins with channel 1. Sequential counters 38 are then used to address the DAC's 30 as the digital words representing the desired amplitude for each generator are transmitted. When the DAC addressing lines 16 are enabled, new current-specifying words are latched into the DAC's, so that new currents are applied to each electrode E. During the read sequence, when the software does not enable the DAC address line, the counter addresses each channel of the multiplexer 20 in sequence and presents the output of each electrode to the voltmeter 22. The ADC 26 input is then read by the software as the desired input data, with a 15 msec interval allowed between successive electrodes.

The special-purpose hardware is driven by "words" or programs written in a FORTH-like language called ASYST (Macmillan Software Co., Inc.). This interactive, flexible programming language is easily adaptable to the requirements of this hardware and is quickly learned by new programmers. One hardware handler word or program accepts a 32-element array of desired currents, verifies that the array is properly scaled, and sends it to the hardware. A second word recovers and stores a 32-element array containing the electrode voltages.

Connection to the electrode array 10 is through four 76 cm. lengths of 24 conductor stripline, each containing the connections for eight electrodes. Each electrode wire is guarded by the two adjacent wires, which are driven by a buffer amplifier from the current generator circuit. This guarding scheme virtually eliminates the effects of inter-wire capacitances due to the cable.

The current generators were calibrated by introducing a single resistor sequentially to each channel. Gain and offset for each channel were thus separately adjusted in software so that by a table look-up function, differences in the channel-to-channel gains could be reduced from the 1% level due to component tolerance to the 1/4096 level achievable by the 12 bit DAC's 30. Similarly, small offsets in the voltmeter circuits were compensated for in software. The variation in current output from the current generators was adjusted to be less than 10 $\mu$A in 5 mA for load changes between one and 800 ohms. The voltmeter multiplexer 20 and A-to-D converter 26 were tested at different read rates. With an interval of 10 msec or greater between successive channels, no influence of one channel on the next was recorded. For faster rates, interactions between successive channels were evident, due to storage in the voltmeter filter. The software therefore drives the voltmeter sequencer with a 15 msec period, so that about ½ second is required to obtain the voltages from all 32 electrodes.

TABLE

| Current Pattern | max $|V^{inho} - V^{homo}|$ | Distinguishability |
|---|---|---|
| TARGET: 22.5 mm DIA CONDUCTOR AT CENTER | | |
| $I^2$ | 2.8760 | 0.4959 |
| 1st iteration | 2.5244 | 1.0691 |
| 2nd iteration | 8.2861 | 2.5208 |
| 3rd iteration | 15.5371 | 2.7336 |
| 4th iteration | 12.0898 | 2.5560 |
| 5th iteration | 12.8418 | 2.6799 |
| 6th iteration | 13.1201 | 2.6157 |
| cos θ | 13.7891 | 2.6281 |
| TARGET: 35.0 mm. DIA CONDUCTOR AT CENTER | | |
| $I^2$ | 0.9570 | 0.3105 |
| 1st iteration | 8.9648 | 3.0135 |
| 2nd iteration | 33.7549 | 6.7895 |
| 3rd iteration | 33.8916 | 6.8037 |
| 4th iteration | 34.6924 | 6.9043 |
| 5th iteration | 32.9102 | 6.7648 |
| 6th iteration | 35.3418 | 6.9099 |

TABLE-continued

| Current Pattern | max $|V^{inho}-V^{homo}|$ | Distinguishability |
|---|---|---|
| cos Θ | 33.3594 | 6.7962 |

TABLE

| Current Pattern | max $|V^{inho}-V^{homo}|$ | Distinguishability |
|---|---|---|
| TARGET: 41.5 mm DIA. CONDUCTOR AT CENTER | | |
| $I^2$ | 1.0840 | 0.4676 |
| 1st iteration | 24.4336 | 6.3529 |
| 2nd iteration | 47.7539 | 9.4739 |
| 3rd iteration | 46.2109 | 9.3497 |
| 4th iteration | 47.9492 | 9.4857 |
| 5th iteration | 50.1855 | 9.3868 |
| cos Θ | 49.4385 | 9.5677 |
| TARGET: 22.5 mm. DIA. CONDUCTOR at (45°, 0.5) | | |
| $I^2$ | 1.4941 | 0.4430 |
| 1st iteration | 6.7139 | 1.5210 |
| 2nd iteration | 16.1426 | 3.2800 |
| 3rd iteration | 15.7617 | 3.3160 |
| 4th iteration | 16.7285 | 3.2766 |
| 5th iteration | 15.4590 | 3.2217 |
| 6th iteration | 17.2314 | 3.2865 |
| 7th iteration | 16.3623 | 3.3170 |

FIG. 2 demonstrates the measured ability of the present system to distinguish inhomogeneities. The absolute value of the maximum difference between the voltages recorded with a target present and with no target present in the tank is plotted as a function of the diameter of the target. The target is placed in the center of the tank. Three different patterns of current were tested. In the right-most, lowest pair of points, the current, $I^2$, is applied between two adjacent electrodes. The points shown were obtained using insulating (open circles) targets. The system can distinguish insulators or conductors from the homogeneous field with equal ability; the voltage differences are positive for insulators, negative for conductors. They are plotted here as absolute values for convenience. Voltage differences above 12 mV were seen when the target diameter was above 120 mm. The middle pair of points was obtained using conducting and insulating targets and a single current, $I^3$, applied between a pair of diametrically opposed electrodes. Because this current pattern results in a larger current density through the center of tank where the target is located, a much larger voltage difference is seen. For example, a voltage difference of 96 mv. is seen with a 120 ml. diameter target. The voltage difference produced by these current patterns is to be compared with the significantly larger voltage differences produced by the best current pattern; $I^1$, shown in the left-most or upper points in FIG. 2. The ability of the present system to distinguish targets can be compared to the results obtainable by a pair of electrodes directly from FIG. 2. For example, using targets of 40 mm in diameter, an electrode pair produces a voltage difference of only about 8–12 mv. when diametrically opposed, and only 3 mv. when adjacent. In contrast, a voltage difference of about 75 mV is obtained from the pair of electrodes at the maximum of the cosine waveform when a cosine pattern of currents is applied. Expressed alternatively, since the resolution of the present system's voltmeter is on the order of ±2.5 mV (full scale is ±5 volts rms), the uppermost points in FIG. 2 shows that targets as small as 8-9 mm in diameter are detectable. It is important to note that these comparisons are all made for targets located at the center of the tank where their detection is most difficult. All of these current patterns will yield greater voltage differences as targets are placed closer to the appropriate electrodes. Since the present system adaptively produces the best current pattern, it will always have a distinguishability greater than that obtainable by either configuration of electrode pairs or by the cosine pattern, which is the best pattern only for concentric targets. The curves in FIG. 2 give the expected results from the theoretical analysis of the experiment performed, obtained by evaluating the first Fourier coefficients of the current patterns $I^k$, and plotting the 1st term of $|\delta V_l^k|$ given by equation (1), for k=1,2,3.

The smallest centered insulators distinguishable from a uniform background of 350 ohm-cm saline for currents $I^1$, $I^2$, $I^3$, are drawn to scale in FIG. 3. These "smallest" targets were found by placing successively smaller targets in the center of the bath until the measured maximum voltage difference was approximately 5 mV.

The experimentally observed diameters 0.9, 2.6 and 8.2 cm. agree closely with the values predicted by formulas (2)–(4).

Although the saline used in these experiments had a resistivity of 385 ohm-cm, the value of resistivity used in the formulas (1) to (4) was 350 ohm-cm. The use of this "effective" resistivity value permits us to model these experiments accurately with the simple formulas.

Figure 5A:
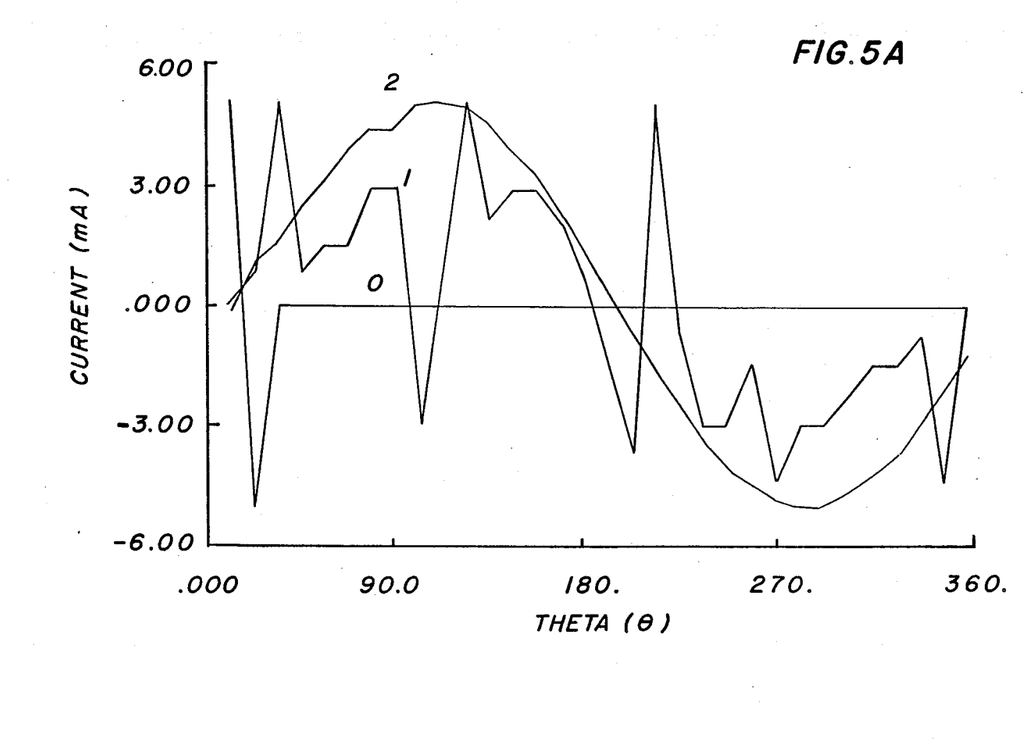
FIG. 5A is a graph plotting the applied current against the angle of the electrode around the tank for three iterations of the inventive method, in the presence of a forty-one millimeter diameter circular conductive target in the center of the tank.
Figure 5B:
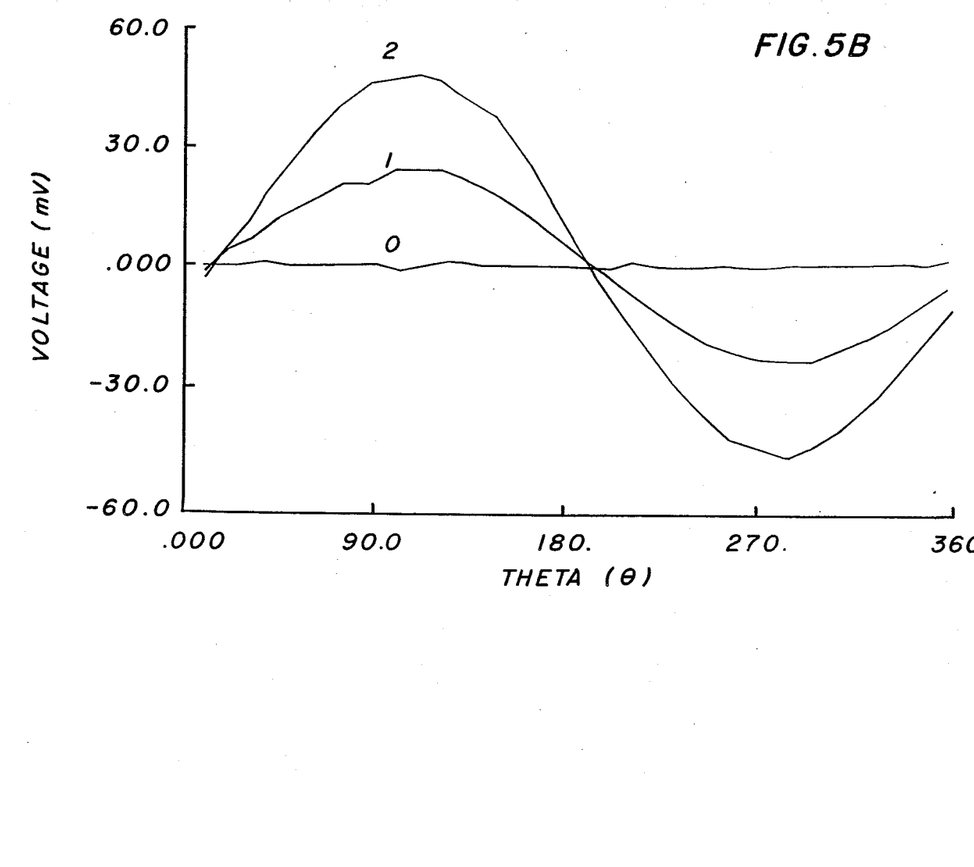
FIG. 5B is a view similar to FIG. 5A plotting the measure of voltage against the angle.

Beginning with a deliberately poor choice of initial current pattern, $I^2$, and a central circular target, the second and subsequent current patterns used where determined by the observed voltage pattern obtained by subtracting the homogeneous voltage pattern from that observed with a target in the tank. The target used was a 41 mm. diameter circular conductive target. The successive voltage patterns found in the first three iterations of the adaptive current scheme are shown in FIGS. 5A and 5B. The successive voltage patterns quickly approached a cosine, which is known to be the best current pattern for this simple case.

Figure 6A:
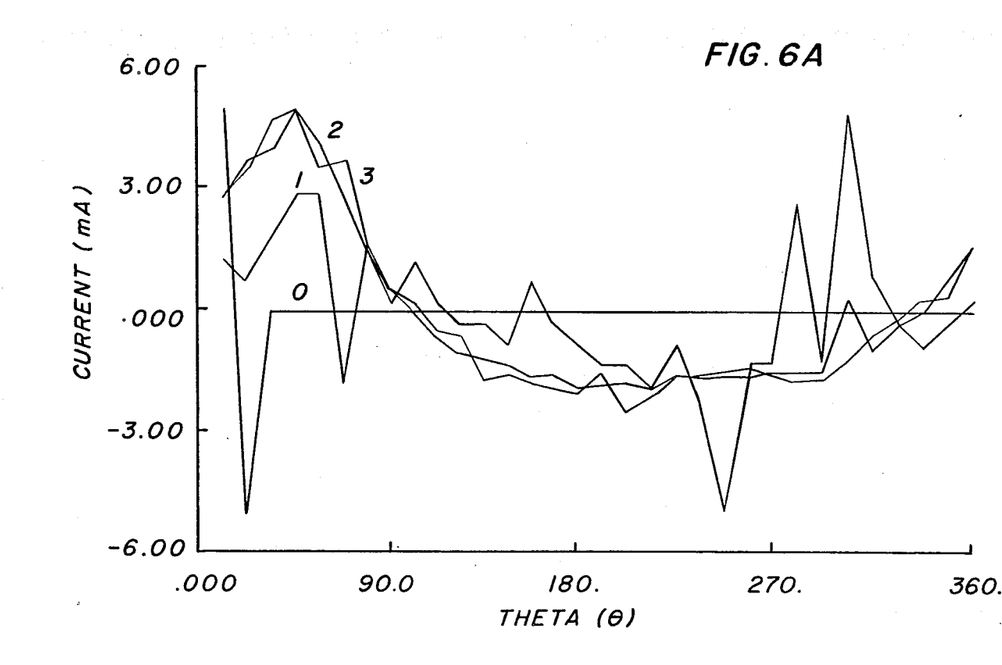
FIG. 6A is a view similar to FIG. 5A for four iterations where the same target was moved to the 45° location at a radius of 0.5 of the tank diameter.
Figure 6B:
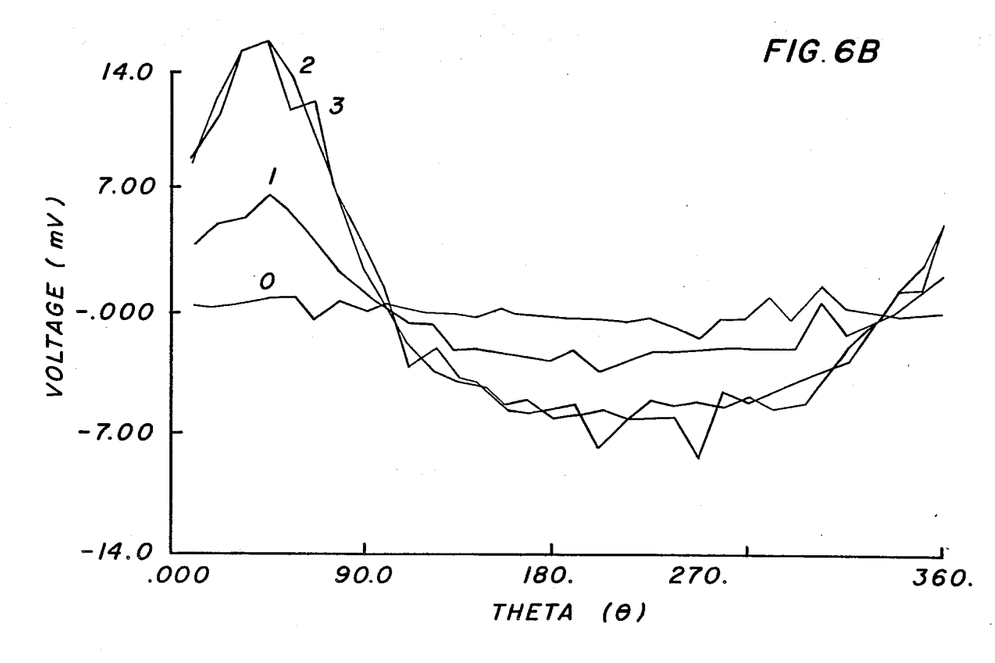
FIG. 6B is a view similar to FIG. 6A plotting the measure of voltage against angle.

In a second test of the adaptive feature, the target was moved from the center of the bath to a location at $\theta=45°$, R=0.5. Beginning with a poor choice of initial current pattern, that of two adjacent active electrodes at $\theta=11°$ and 23°, the iterative scheme was again allowed to determine subsequent current patterns. These successive current patterns are shown in FIG. 6A. The voltage patterns (FIG. 6B) and the resulting current pattern for the next iteration (FIG. 6A) approach a maximum on the electrode located nearest the target. The current pattern becomes smoother than the original guess and is of relatively low amplitude where the bath is homogeneous. In other words, the applied current is maximized near the inhomogeneity or target.

The TABLE gives the values of the maximum voltage differences and distinguishabilities for each iteration of the adaptive process when it was applied to four targets in a 285 ohm-cm solution. The starting current pattern was $I^2$. Since the smallest measurable voltage is ±2.5 mV, differences in voltage below 5 mV are below the precision of the system.

FIG. 7 is a flow chart of the inventive method.

The invention claimed is:

1. In an electrical current computed imaging system, having a selected precision for the smallest voltage difference the system can measure in an array of electrodes on the surface of a body, a method of producing the best current pattern for applying to the array to distinguish between an unknown conductivity($\sigma$) inside the body and a selected conductivity(s), comprising:
- (a) applying an arbitrary current pattern ($I^k$) to the array to generate a voltage pattern ($V^k(\sigma)$) on the array for the unknown conductivity;
- (b) measuring the voltage pattern for the unknown conductivity;
- (c) calculating a voltage pattern ($V^k(s)$) for the selected conductivity;
- (d) calculating the difference ($\delta V^k$) between the values $V^k(\sigma)$ and $V^k(s)$, according to the formulas:

$$\delta V^k \equiv V^k(\sigma) - V^k(s)$$

and where L is the total number of electrodes 1 in the array;
- (e) calculating a new current pattern ($I^{k+1}$) according to the equation;

$$I^{k+1} = \delta V^k / ||\delta V^k||$$

$$\text{where } ||\delta V^k|| = \left[ \sum_{l=1}^{L} (\delta V_l^k)^2 \right]^{\frac{1}{2}} \text{; and}$$

- (f) if the absolute value of the difference between the arbitrary current pattern and the new current pattern is equal to or less than the selected precision, applying the arbitrary current pattern to the array of electrodes as the best current pattern, and if the absolute value of the difference between the arbitrary current pattern and the new current pattern is greater than the selected precision, applying the new current pattern to the array of electrodes and repeating steps (b) through (f), until the difference between the absolute value of the new current pattern and a preceding current pattern is equal to or less than the selected precision.

2. The method of claim 1, including arranging the array of electrodes circumferentially around a container, containing the body.

3. In an electrical current computed imaging system, having a selected precision for the smallest voltage difference the system can measure in an array of electrodes on the surface of a body, an apparatus for producing the best current pattern for applying to the array to distinguish between an unknown conductivity($\sigma$) inside the body and a selected conductivity(s), comprising:

- (a) means for applying a selected current pattern ($I^k$) to the array to generate a voltage pattern ($V^k(\sigma)$) on the array for the unknown conductivity;
- (b) means for measuring the voltage pattern for the unknown conductivity;
- (c) means for calculating a voltage pattern ($V^k(s)$) for the selected conductivity;
- (d) means for calculating the difference between the values $V^k(\sigma)$ and $V^k(s)$, according to the formulas: $\delta V^k \equiv V^k(\sigma) - V^k(s)$ and where L is the total number of electrodes 1 in the array;
- (e) means of calculating a new current pattern ($I^{k+1}$) according to the equation;

$$I^{k+1} = \delta V^k / ||\delta V^k||$$

$$\text{where } ||\delta V^k|| = \left[ \sum_{l=1}^{L} (\delta V_l^k)^2 \right]^{1/2} \text{; and}$$

- (f) means for determining if the absolute value of the difference between the selected current pattern and the new current pattern is equal to or less than the selected precision, wherein said applying means continues to apply the selected current pattern to the array of electrodes as the best current pattern if the absolute value of the difference between the selected current pattern and the new current pattern is less than or equal to the selected precision, and wherein said applying means applies the new current pattern to the array of electrodes if the absolute value of the difference between the selected current pattern and the new current pattern is greater than the selected precision, said determining means causing said voltage pattern measuring means, said voltage pattern calculating means, said difference calculating means and said new current pattern calculating means to repeat their function using said new current pattern until the difference between the selected current pattern and the new current pattern is equal to or less than the selected precision.

* * * * *